United States Patent [19]
Koch

[11] Patent Number: 5,263,742
[45] Date of Patent: Nov. 23, 1993

[54] FINGERPRINTING SYSTEM AND METHOD

[76] Inventor: John J. Koch, 10879 Hematite Mapaville Rd., Festus, Mo. 63028

[21] Appl. No.: 831,917

[22] Filed: Feb. 6, 1992

Related U.S. Application Data

[62] Division of Ser. No. 439,605, Nov. 20, 1989, Pat. No.

[51] Int. Cl.$^5$ ............................................. B42D 15/00
[52] U.S. Cl. ..................................... 283/78; 283/69; 283/57; 283/58; 283/105
[58] Field of Search ........................ 283/57, 58, 68, 69, 283/78, 105

[56] References Cited

U.S. PATENT DOCUMENTS

| | | | |
|---|---|---|---|
| 878,366 | 2/1908 | Evans | 283/78 X |
| 1,374,208 | 4/1921 | Jones | 283/69 X |
| 1,561,069 | 11/1925 | Fittall | 283/105 X |
| 2,500,612 | 3/1950 | Krogh | 283/69 X |
| 2,912,259 | 11/1959 | Young | 283/78 |
| 3,258,277 | 6/1966 | Schuster | 283/58 X |
| 3,447,818 | 6/1969 | De Pizzol | 283/68 |
| 3,664,910 | 5/1972 | Hollie | 283/69 X |
| 3,709,524 | 1/1973 | McKee et al. | 283/78 X |
| 4,179,139 | 12/1979 | Savar et al. | 283/58 X |
| 4,943,089 | 7/1990 | Reardon | 283/68 X |
| 5,067,749 | 11/1991 | Land | 283/68 X |

FOREIGN PATENT DOCUMENTS 2147541  5/1985  United Kingdom ................ 283/58

*Primary Examiner*—Paul A. Bell
*Attorney, Agent, or Firm*—Grace J. Fishel

[57] ABSTRACT

A system and method for taking and developing a fingerprint wherein the subject's fingers are not dirtied or exposed to chemicals. The fingerprint is recorded on a layer of adhesive adhered to a sheet of transparent material. The print is developed by making a copy of it on a sensitized surface by back reflecting radiant energy through the adhesive whereby the print is imaged.

10 Claims, 3 Drawing Sheets

FINGERPRINTING SYSTEM AND METHOD

This is a continuation, of application Ser. No. 07/439,605, filed Nov. 20, 1989. Now U.S. Pat. No. 5,114,188.

BACKGROUND OF THE INVENTION

The present invention relates to a system and method for obtaining the fingerprints of a person filing an application such as for employment, credit, license, identification or the like. It can also be used for obtaining the fingerprints of a person presenting a credit card or a check for payment, whereby such person may be accurately identified irrespective of the name or names he is using should the negotiable instrument prove to be worthless or the information on the application false.

The use of fingerprints for identification purposes is based upon distinctive ridge outlines which appear on the bulbs on the inside of the end joints of the fingers and thumbs. Comparable marks also occur on the feet. These ridges have definite contours and appear in several general pattern types,, each with general and specific variations of the pattern, dependent on the shape and relationship of the ridges. A fingerprint can be classified according to its pattern type and this data can be systematically searched.

The Federal Bureau of Investigation maintains a Criminal File of fingerprint information and an even larger Civil File. The Criminal File is a potent factor in obtaining the apprehension of fugitives who might otherwise escape arrest and the Civil File is an invaluable aid in identifying missing persons and unknown deceased. In the latter category, the victims of major disasters may be quickly and positively identified if their fingerprints are on file, thus providing a humanitarian benefit not usually associated with fingerprint records.

The vast majority of persons have never been fingerprinted because the present system is too cumbersome and objectionable to be in common use. More particularly, with present day procedures, printer's ink is rolled out on a piece of glass or other hard surface, the fingers and/or hand of the individual to be fingerprinted are pressed upon the film of printer's ink and the hand or fingers are then placed upon a sheet of paper and an impression is made to form a record. The individual then cleans the ink off his hands with soap and water or with an appropriate solvent. The record is processed by classification and photographed if additional copies are required.

Even with a skilled operator, from time to time various problems arise in taking inked impressions. Indistinct or illegible prints are usually caused by one or more of the following factors: Failure to reproduce the focal points because the finger has not been fully rolled from one side to the other, and the bulb of the finger from joint to tip has not been completely inked. Allowing the fingers to slip or twist will result in smears, blurs and false-appearing patterns. Failure to thoroughly clean the fingers or inking apparatus of foreign substances and perspiration causes the appearance of false markings and the disappearance of ridge characteristics. Insufficient ink or too much ink obliterates or obscures the ridges. There are also considerable problems associated with taking fingerprints from the dead due to stiffening of the fingers or removal of oils from the skin if the body has been soaked.

Various chemical systems have been proposed to overcome the shortcomings associated with inked impressions. For example, U. S. Pat. No. 2,500,612 to Krogh describes a system where the subject dips his fingertip in a colored powder and then touches it to a strip of tape having a coating of adhesive material. The powder in this system interferes with the impression and is itself objectionable to the subject who is left "red handed" at least on his fingertips.

Another inkless system is described in U. S. Pat. No. 3,664,910 to Hollie in which a fingerprint is taken in an adhesive layer on a strip of plastic. The print is invisible on the adhesive surface and is not made visible until it is photographed under ultraviolet light.

Adhesive tape has also been used to lift fingerprints which have been made visible by dusting them with powder. Both rubber and transparent tape is available for this purpose in a variety of sizes. The adhesive surface is typically protected with a celluloid cover which is removed before the lift is made. White tapes are obviously used to pick up prints dusted with dark or metal powders and black tapes with light colored powders.

In view of the above, there is a need for an inkless fingerprinting system and method which does not dirty the hands of the subject and which can be readily developed in the absence of sophisticated ultraviolet cameras or the like. It is also an object to provide a system and method which makes provision for cleaning the fingers of the subject of any foreign material which would interfere with taking the print. It is therefore an object of the present invention to provide a system and method satisfying the above mentioned objectives. Other objects and features of the invention will be in part apparent and in part pointed out hereinafter.

The invention accordingly comprises the constructions and methods hereinafter described and their equivalents, the scope of the invention being indicated in the following claims.

SUMMARY OF THE INVENTION

A fingerprinting system has a sheet of transparent material coated with a film of adhesive sensitive to record a fingerprint. Means are provided for back reflecting radiant energy for developing the print and making a copy of it on a sensitized surface. The counterpart method involves taking a fingerprint on a sheet of transparent material coated with a film of adhesive sensitive to record a fingerprint and then making a copy on a sensitized surface by back reflecting radiant energy through the adhesive. As the radiant energy passes back through the adhesive, the fingerprint is imaged on the sensitized surface.

BRIEF DESCRIPTION OF THE DRAWINGS

In the accompanying drawings, in which several of various possible embodiments of the invention are illustrated, corresponding reference characters refer to corresponding parts throughout the several views of the drawings and in which.

DETAILED DESCRIPTION OF THE INVENTION

Figure 1:
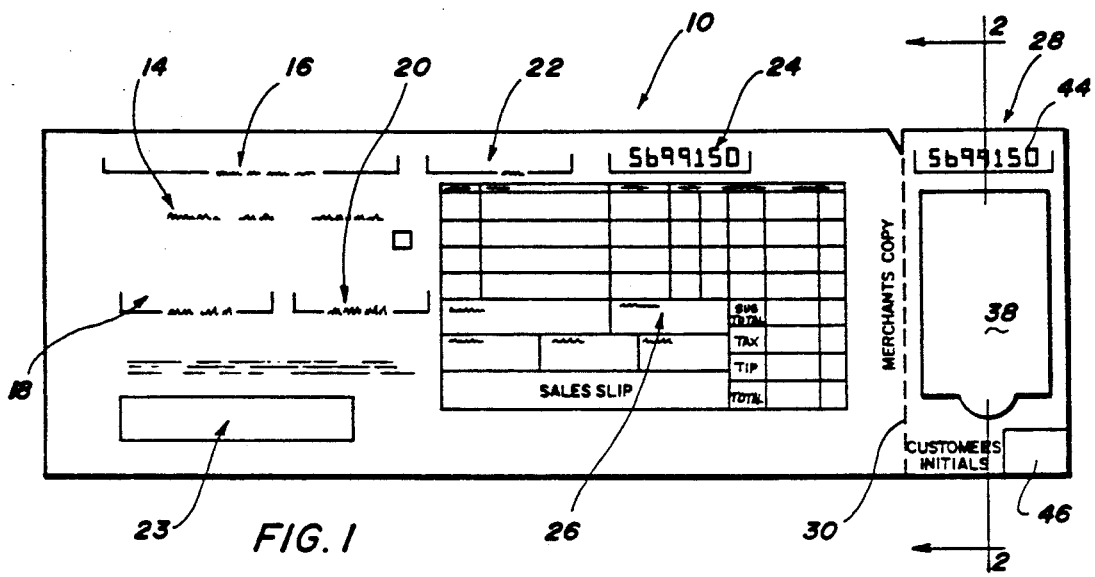
FIG. 1 is a plan view showing a credit card invoice with a tab extension for taking fingerprints in accordance with the present invention.

Referring to the drawings by reference character, reference numeral 10 refers to a credit card invoice, as shown in FIG. 1. As is well known, the original copy of invoice 10 is usually retained by the vendor, the second copy is given to the purchaser and the third or hard copy (so-called because it is made of stiff card stock) is sent to the bank. Sometimes the original copy is given to the purchaser and the second copy is retained by the merchant. The bank copy of invoice 10 is subsequently sent to the credit card company for payment and ultimately the sale is charged to the purchaser's account. The original copy, second copy and bank copy may be made of carbonless paper or carbon paper may be inserted between the original and second copy and between the second and third copy.

Invoice 10 has the usual space to receive credit card indicia, thereby printing the customer's name 14 and account number 16. Also printed on the invoice at the time of sale are the vendor's account number 18, the date of the transaction 20 and the sales amount 22. A space 23 is provided for the customer's signature and other spaces are provided for handwriting or printing details of the transaction (not shown) such as quantity, description, color, size, unit cost and so forth. Each invoice 10 is provided with a number 24 assigned by the credit card company and with a space 26 in which the vendor can write an authorization code.

Above a certain dollar amount, the vendor is required to call the credit card company for authorization prior to accepting the charge, otherwise the risk of loss is on the vendor in the event that the charge is not honored. From the credit card company's standpoint, it has no way of knowing whether the charge card is being properly used at the time the authorization code is requested by the vendor unless the charge card has been previously reported as lost or stolen. Hence it can merely confirm that the charge is within the credit limit of the account holder. If the card turns out to be stolen or otherwise misused, the risk of loss is on the credit card company. This shifting of the loss is advantageous to the vendor but the vendor pays for this service as a percentage of the sales amount for each transaction passed through to the credit card company. It is therefore beneficial indirectly to the vendor who must ultimately bear the cost in fees paid to the credit card company to minimize the number of invalid charges.

Figure 3:
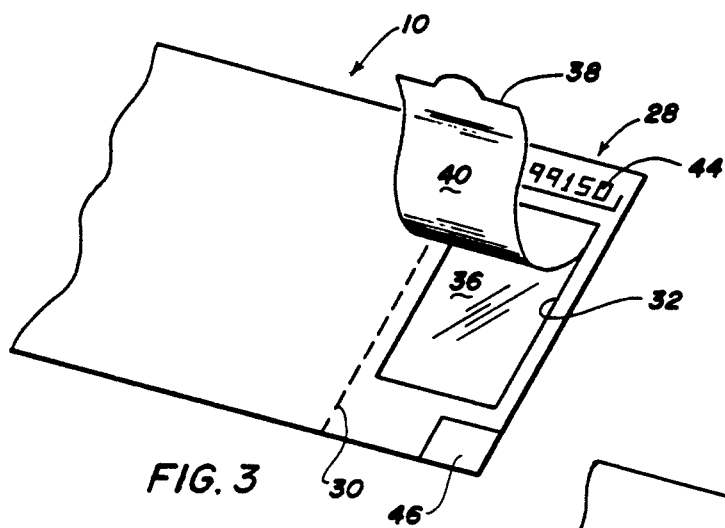
FIG. 3 is a fragmentary perspective view of the tab extension showing a protective strip in process of being peeled away from a thin sheet of material forming a window coated with an adhesive layer.
Figure 4:
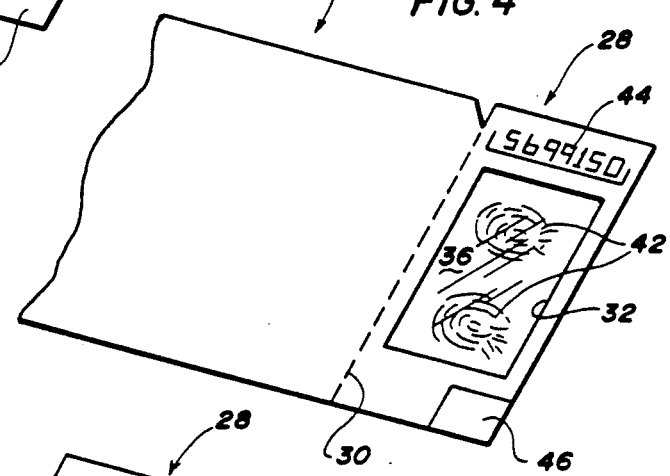
FIG. 4 is a view similar to FIG. 3 but with the protective strip peeled away and with an impression of a right and left thumb in the adhesive layer.
Figure 5:
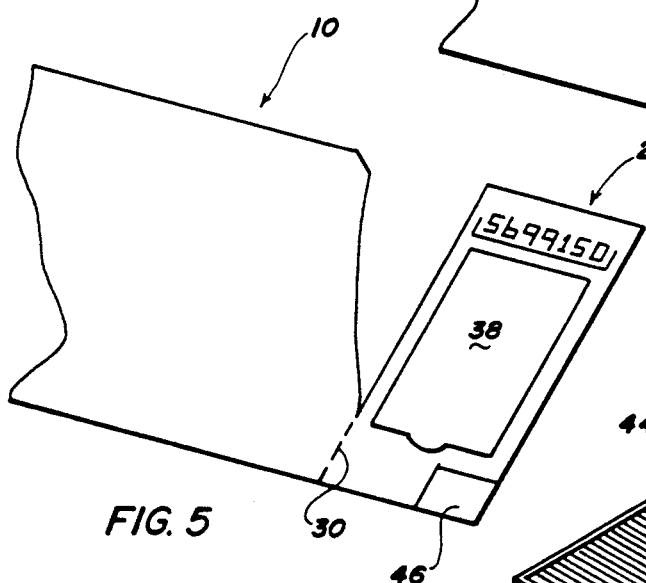
FIG. 5 is a view similar to FIGS. 3 and 4 but with the protective strip reinstalled on the adhesive layer and with the tab extension broken away from the invoice.
Figure 6:
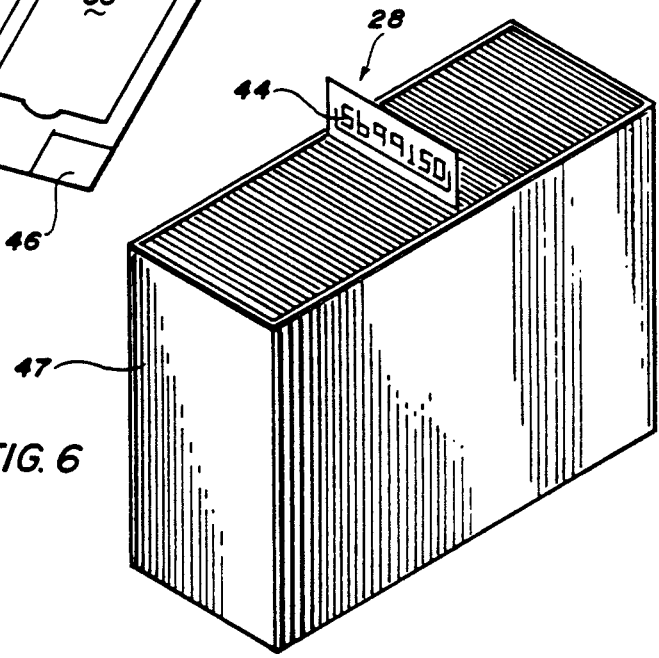
FIG. 6 is a perspective view of a tray suitable for filing the tab extension.

As shown in FIGS. 1 and 3-5, an extension tab 28 is made of the same card stock as the bank's copy of the invoice. A line of perforations 30, best seen in FIGS. 3-5, is provided for separating extension tab 28 from invoice 10 as more particularly described hereinafter.

Figure 2:
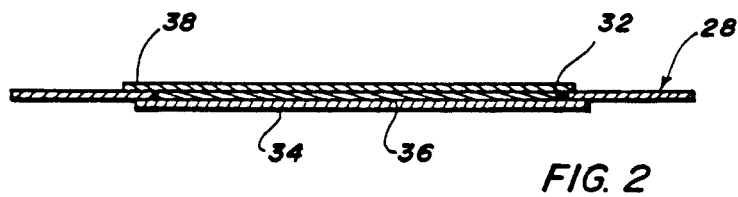
FIG. 2 is an enlarged sectional view taken along line 2—2 in FIG. 1.

Tab 28 includes a window 32 which is covered with a thin sheet 34 of substantially transparent material. Suitable transparent materials include plastics such as polyethylene terephthalate sold under the trademark MYLAR, polyvinyl chloride and the like. As shown in FIG. 2, sheet 34 is slightly larger than window 32 and is glued or otherwise attached to the underside of tab 28. It is important that sheet 34 be strong enough to receive a fingerprint without breaking though and be capable of developing a print in the manner described below. By way of example, a sheet having a thickness in the order of 1 mil to 10 mil is adequate when the sheet of is made of MYLAR, preferably about 4 mil to 5 mil as thinner films tend to stick to the subject's fingers and wrinkle.

A thin film of adhesive 36 sensitive to record a fingerprint is adhesively engaged to sheet 34 to such extent that it not be lifted from the sheet when the fingerprint is made or comes off on the subject. Adhesive 36 must be pliable enough to take a print yet rigid enough to hold a crisp image so that the print is refined and clear. To preserve this quality, a protective strip 38 is applied to adhesive 36 to keep it from drying and to prevent it from collecting foreign matter. Surface 40 of strip 38 which contacts adhesive 36 is treated with silicone or wax such that it parts cleanly from the adhesive layer without lifting it from sheet 34. Adhesive layer 36 must be thin enough so that light can be reflected through it during the process of developing the print as described below. One suitable material for this purpose is V-23 Adhesive sold by Budnick, Inc. of St. Louis, Missouri. V-23 is a thermoset acrylic copolymer and can be effectively used in the present invention in a layer from 1 mil to 2 mil thick.

As illustrated in FIG. 4, extension tab 28 is sized such that right and left thumb prints 42 can be recorded in adhesive layer 36. Alternatively, two impressions of the same finger can be taken. This has the advantage of removing any foreign material in the first print which is on the subject's finger that might otherwise spoil the identification. A number 44 is printed at the top edge of tab 28 corresponding to number 24 printed on invoice 10. A space 46 is provided for the customer's initials.

In use, invoice 10 is filled out in the usual manner, protective strip 38 is peeled back and the invoice with tab 28 attached is handed to the customer. The customer signs his name in space 23, presses his right and left thumbs into adhesive 36, initials space 46 and hands the invoice back to the vendor. The vendor then checks that the invoice has been signed, space 46 initialed and prints 42 are visible in adhesive 36 by viewing them at a low angle. Protective strip 38 is then reattached and tab 28 broken away from invoice 10 at line of perforations 30 as shown in FIG. 5.

The bank copy of invoice 10 is presented to the credit card company for payment and tab 28 is filed in a suitable storage device 47 for retrieval on the basis of number 44. If the charge is good, tab 28 is eventually thrown away but if the charge is bad, tab 28 is sent to the credit card company for use in identifying the person misusing the charge card.

Figure 7:
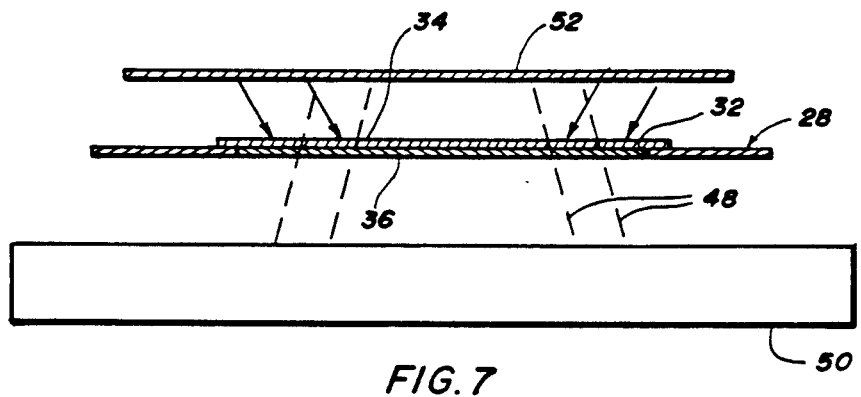
FIG. 7 is a sectional view on the same scale as FIG. 2 showing a fingerprint on the tab extension being developed.

The development of a latent print on tab 28 in accordance with the present invention is illustrated in FIG. 7. As shown, prints 42 can be developed by making a copy on a sensitized surface (generally paper, film, metal plate or the like) by action of radiant energy 48 which is back reflected through adhesive 36. A suitable piece of equipment for this purpose is a photocopy machine 50 such as a Cannon copier. Means for back reflecting the radiant energy 52 include a mirror, polished metal surface of aluminum, tin, silver and the like and other polished dark surfaces which will copy black.

The fingerprint system and method of the present invention has broad application and can be used in connection with checks and other negotiable instruments in additional to credit cards. It can also be used in connection with applications for employment, credit, license, identification or the like.

Figure 8:
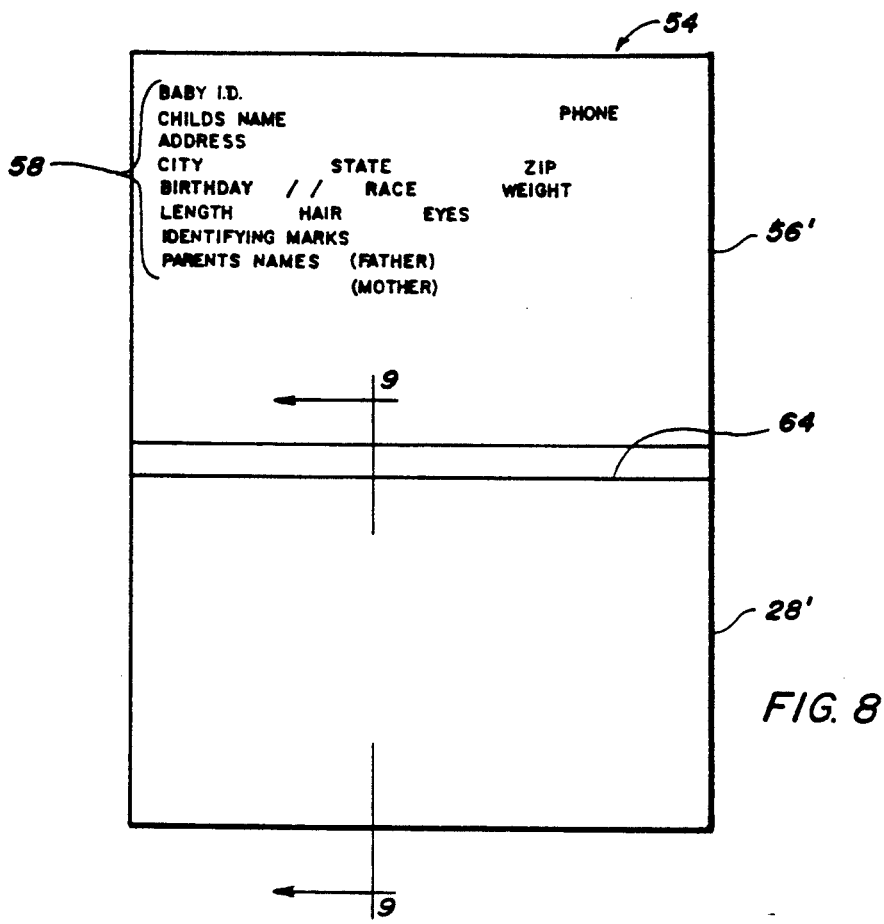
FIG. 8 is a plan view showing a baby identification with a tab extension having a protective cover for taking a foot impression in accordance with the present invention.
Figure 9:
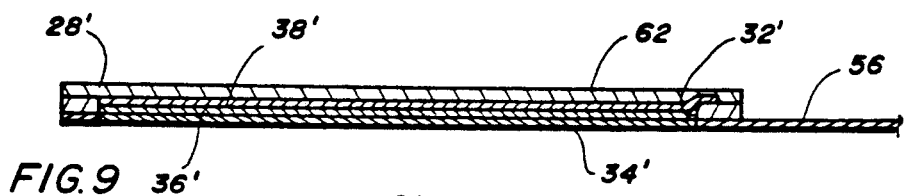
FIG. 9 is an enlarged sectional view taken along line 9—9 in FIG. 8.
Figure 10:
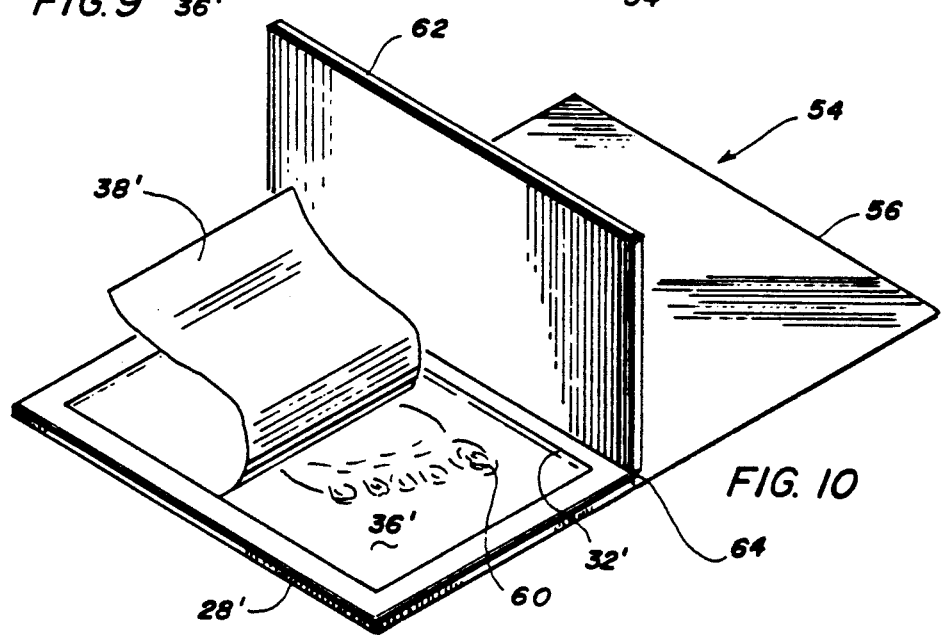
FIG. 10 is a perspective view showing a protective strip being peeled away from a thin sheet of material forming a window coated with an adhesive layer for taking an impression of a baby's foot.

Referring to FIGS. 8-10, a baby ID 54 includes a card 56 with space 58 for generally recording relevant personal and physical information. An enlarged extension tab 28' made of thick cardboard is attached to card 56. Tab 28' includes a window 32' at the back of which is attached a thin sheet 34' of substantially transparent material. A thin film of adhesive 36' is provided on sheet 34' for recording a footprint 60. A peel away strip 38' is provided for protecting adhesive 36' prior to use and a cardboard cover 62 hinged at 64 along the line of attachment between tab 28' and card 56. This arrangement is preferred when footprint 60 is to be kept for an extended period of time.

Footprint 60 can be taken in adhesive 36' and the print developed in the same manner as fingerprints 42 on invoice 10. Hence as used throughout the claims the word "fingerprinting" includes foot printing as the feet have distinctive ridges in the same manner as the hands.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed is:

1. A fingerprinting system comprising
    a sheet of transparent material coated with a film of adhesive sensitive to record a fingerprint,
    a means for back reflecting radiant energy and
    a means for making a copy of the fingerprint on a sensitized surface,
    said means for back reflecting radiant energy reflecting said energy to said means for making a copy.

2. The system of claim 1 wherein the means for back reflecting the radiant energy is a mirror.

3. The system of claim 1 wherein the means for back reflecting the radiant energy is a polished metal surface.

4. The system of claim 1 wherein the means for back reflecting the radiant energy is a polished dark surface which will copy black.

5. A fingerprinting system for a credit card invoice comprising
    an extension tab attached to the invoice and separable from the invoice by means of perforations, said extension tab having a window covered with a thin sheet of substantially transparent material, an adhesive sensitive to record a fingerprint adhesively engaged to the sheet,
    a means for back reflecting radiant energy through the adhesive and
    a means for making a copy of the fingerprint on a sensitized surface,
    said invoice and said extension tab having indicia for correlating them and said means for back reflecting radiant energy reflecting said energy to said means for making a copy.

6. The system of claim 5 wherein the means for back reflecting the radiant energy is a member selected from the group consisting of a mirror, a polished metal surface and a polished dark surface which will copy black and wherein the means for making the copy is a photocopy machine.

7. The system of claim 6 wherein the sheet of substantially transparent material is made of polyethylene terephthalate and is from 1 mil to 10 mil thick.

8. The system of claim 7 wherein the sheet of substantially transparent material is from 4 mil to 5 mil thick.

9. The system of claim 7 wherein the adhesive layer is from 1 mil to 2 mil thick.

10. The system of claim 9 wherein the adhesive is a thermoset acrylic copolymer.

* * * * *